United States Patent
Offermanns (10) Patent No.: US 12,208,186 B2
(45) Date of Patent: Jan. 28, 2025

(54) EXTRACORPOREAL BLOOD TREATMENT DEVICE

(71) Applicant: Fresenius Medical Care Deutschland GmbH, Bad Homburg (DE)

(72) Inventor: Lars Offermanns, Butzbach (DE)

(73) Assignee: FRESENIUS MEDICAL CARE DEUTSCHLAND GMBH, Bad Homburg (GB)

(*) Notice: Subject to any disclaimer, the term of this patent is extended or adjusted under 35 U.S.C. 154(b) by 710 days.

(21) Appl. No.: 17/275,285

(22) PCT Filed: Sep. 16, 2019

(86) PCT No.: PCT/EP2019/074661
§ 371 (c)(1),
(2) Date: Mar. 11, 2021

(87) PCT Pub. No.: WO2020/053442
PCT Pub. Date: Mar. 19, 2020

(65) Prior Publication Data
US 2022/0040388 A1 Feb. 10, 2022

(30) Foreign Application Priority Data
Sep. 14, 2018 (DE) .......................... 102018122583.0

(51) Int. Cl.
*A61M 1/16* (2006.01)
*A61M 1/34* (2006.01)
*A61M 39/28* (2006.01)

(52) U.S. Cl.
CPC ........ *A61M 1/1601* (2014.02); *A61M 1/3413* (2013.01); *A61M 1/342* (2013.01); *A61M 39/281* (2013.01); *A61M 2205/18* (2013.01); *A61M 2205/3331* (2013.01); *A61M 2205/3334* (2013.01); *A61M 2205/502* (2013.01)

(58) Field of Classification Search
CPC .................................................. A61M 2205/14
See application file for complete search history.

(56) References Cited

U.S. PATENT DOCUMENTS 6,468,424 B1* 10/2002 Donig ................. A61M 1/1668
210/321.71
2019/0001057 A1* 1/2019 Tsoukalis ........... G06K 7/10366

FOREIGN PATENT DOCUMENTS

DE 19605260 11/1996
DE 102007024463 11/2008
(Continued)

*Primary Examiner* — Benjamin M Kurtz
(74) *Attorney, Agent, or Firm* — Jacobson Holman PLLC (57) ABSTRACT

The present invention pertains to an extracorporeal blood treatment device (1), preferably a hemodialysis device, hemofiltration device, or hemodiafiltration device, comprising a fluidic system (2) having a connection point (20) for adding substances, a detection arrangement (4) for detecting a flow of a substance at the connection point (20), wherein the detection arrangement is configured to generate a flow signal, when a flow of a substance is detected at the connection point (20), and a control unit (5), which is communicatively connected to the detection arrangement (4). The control unit (5) is furthermore configured to output a signal (50) in reaction to a received flow signal. The present invention furthermore pertains to a corresponding method for monitoring at least one connection point.

14 Claims, 3 Drawing Sheets

(56) References Cited

FOREIGN PATENT DOCUMENTS

| | | |
|---|---|---|
| DE | 102007044413 | 3/2009 |
| DE | 102014010306 | 1/2016 |
| EP | 2150293 | 2/2010 |
| WO | WO2013138537 | 9/2013 |

* cited by examiner

EXTRACORPOREAL BLOOD TREATMENT DEVICE

TECHNICAL FIELD

The invention relates to an extracorporeal blood treatment device and a method for monitoring a connection point of an extracorporeal blood treatment device.

TECHNOLOGICAL BACKGROUND

From the prior art extracorporeal blood treatment devices for the treatment of patients are known, for example, for performing a dialysis. The extracorporeal blood treatment devices generally comprise fluidic systems through which both the blood of the patient and further substances that are relevant for the treatment of the patient may flow. The fluidic systems may be formed e.g. in the form of tube or of tubular systems that may transport both patient blood and a dialysis liquid. With these fluidic systems medical liquids may be fed to the patient and/or blood may be withdrawn from the patient. Such tube systems form complex systems, in particular in combination with the corresponding treatment device.

Such fluidic systems and in particular tube sets often comprise connection points, which allow the addition or administering of additional substances, e.g. medicaments or other infusion solutions, during a treatment. Such connection points are generally closed during normal operation or at least at the start of the treatment, however, may be optionally used. For this purpose, e.g. syringes or bags or further conduits that are provided with an adding device such as e.g. a syringe pump are coupled to the connection points, such that the respective substance may accordingly be administered to the patient via the connection point.

In this regard it is problematic that, in particular in more complex systems, the risk is present that a user does not use the correct connection point that is suitable for the intended purpose, but instead inadvertently uses a connection point arranged at another position, thereby potentially posing a hazard to the patient. For example, an entire medicament may enter the blood circuit of the patient in a very short time instead of being continuously administered. This may also lead to a situation, wherein a medicament is administered in the wrong fluidic system. For example, a cleaning or rinsing liquid may enter the blood circulation of the patient instead of the dialysate circuit or a medicament may not at all enter the blood circuit of the patient, when it is instead fed into the dialysate circuit.

To monitor the correct course of a flow in simple infusion systems a corresponding measurement method is known from e.g. WO 2013/138537 A1, which outputs optical or acoustic signals in the case of a failure or erroneous functioning, wherein furthermore a subsequent control of the flow based on the flow measurement is possible.

Adding devices are also known e.g. from EP 2 150 293 A1, which examine or check a correct coupling by means of a pressure measurement. A monitoring of the correct functioning of an adding device by means of a pressure measurement is furthermore known from DE 10 207 044 413 A1.

However, by examining or checking the correct functioning or the correct fluid flow or perfusion speed it is not checked whether the adding of a substance occurs at an intended or predetermined position for said substance, such that in this regard further improvements are required to increase the safety of the patient.

SUMMARY OF THE INVENTION

Starting from the known prior art, it is an object of the present invention to provide an improved device for monitoring of connection points as well as a corresponding method.

Said object is achieved by an extracorporeal blood treatment device, preferably a hemodialysis device, hemofiltration device, or hemodiafiltration device, comprising: a fluidic system (2) having a connection point (20) for adding substances; a detection arrangement (4) for detecting a flow of a substance at the connection point (20), wherein the detection arrangement is configured to generate a flow signal, when a flow of a substance is detected at the connection point (20); a control unit (5), which is communicatively connected to the detection arrangement (4) and is configured to output a signal (50) in reaction to a received flow signal. Preferred embodiments are indicated in the present description and Figures.

Accordingly, an extracorporeal blood treatment device is suggested, which comprises a fluidic system having at least one connection point for adding substances and at least one detection arrangement for detecting a flow of a substance at the connection point, wherein the detection arrangement is configured to generate a flow signal, when a flow of a substance is detected at the connection point, and a control unit, which is communicatively connected to the detection arrangement and is configured to output a signal in reaction to a received flow signal.

The outputting of the signal based on the detected flow of a substance has the advantage that, when an addition is carried out, the attention of a user of the extracorporeal blood treatment device is drawn to the fact that a substance is added at the corresponding connection point. Accordingly, a potentially inadvertent addition of a substance may e.g. be avoided and/or it may e.g. be ensured that the addition on itself is allowed and occurs at a suitable point of the fluidic system.

In other words, the addition of a substance at a connection point may be monitored, such that the occurrence of situations that may be potentially detrimental for a patient may be avoided and at the same time a desirable therapeutic effect may be guaranteed. This is particularly advantageous in the case of an addition of substances at connection points that are directly connected to the extracorporeal blood circulation of a patient, since a direct infusion of a substance in the bloodstream of the patient may pose an increased risk or hazard for the patient, when this is not desirable.

By outputting of the signal the attention of the user or operator of the connection point of the extracorporeal blood treatment device, for example, medical personnel, is immediately drawn to the respective usage to hence provide support during the operation or setup of the extracorporeal blood treatment device. For example, it may thereby be ensured that the substance is connected to the correct connection point in the fluidic system and/or at a provided pump, such that e.g. a predetermined pump rate or perfusion rate may be maintained and/or the patient is provided with the prescribed or required dosage of a medicament. The outputting of the signal may accordingly occur during operation as well as in an interrupted or inactive state of the extracorporeal blood treatment device.

As extracorporeal blood treatment devices, various devices are known, which withdraw blood from a patient, e.g. via an arterial access, process, for example, purify, divide and/or separate, bypass, oxygenate, de-acidify, and/or dialyze the withdrawn blood, and subsequently return the blood to the patient, e.g. via a venous access. The fluidic system may in the simplest embodiment be provided, e.g. as a simple tube or tube connection, however, may also comprise a tube system, wherein various branching points and/or tube connections may be provided. For example, the fluidic system may form a circuit, wherein one or more connection points are provided at the circuit. Alternatively, or in addition, the fluidic system may also comprise reservoirs, containers, bags, and/or pumps, or may be exclusively formed thereof. Accordingly, a connection point may be provided as a fluid coupling, for example, as a Luer-lock connection or self-sealing membrane, both directly and indirectly, for example, with a tube connection.

The substances that may be added are generally understood as comprising all substances, which cause an indirect or direct therapeutic effect in the treatment of the patient that has been or is to be performed. As such, the substances may comprise medical fluids, for example medicaments such as blood pressure stabilizers, anti-inflammatory drugs, painkillers, and substitution liquids, such as e.g. saline solutions, and/or liquids for therapeutic secondary symptoms, such as e.g. glucose, heparin, or insulin. Examples for liquids having an indirect therapeutic effect may also comprise substitution liquids, such as saline solutions or glucose, however, may also be provided as a dialysis liquid, or, in the simplest form, water.

The detection arrangement may be formed as one or more units, wherein the at least one unit is either provided for a single connection point or for multiple connection points. For example, a unit may be formed, such that said unit detects or determines the flow of a substance into adjacent connections and forwards the respective flow of a substance to the control unit via a corresponding flow signal. By the same token, a plurality of units may be provided, wherein each unit determines the flow of a substance of a respective connection point and forwards said flow via a corresponding switch or circuitry to the control unit, either directly or via a central detection unit.

Due to the detection of a flow of a substance a usage or operation of the connection point may be detected. Accordingly, it may be determined whether the connection point is active or inactive. Preferably, the detected flow of a substance allows that a conclusion or assessment regarding the respective usage may be derived, for example, relating to the type, duration, or extent of the usage.

In order to output a signal corresponding to the detected flow of a substance a control unit is furthermore provided, which provides e.g. a logical level for the processing of flow signals. For example, the control unit may comprise a processor or microprocessor and/or a corresponding circuitry, which evaluates or processes the received flow signals and accordingly triggers the outputting of a signal by a corresponding control. The flow signal may hence be an information or a signal corresponding to the detected flow of a substance. Depending on the arrangement or embodiment of the detection arrangement and/or the fluidic system or the one or more connection points, or generally the complexity inherent to the required monitoring of the connection points, the control unit may be separated from the detection arrangement or may be combined with the detection arrangement as a unit.

In order to draw the attention of a user or operator to the performed operation at the connection point or to indicate that a flow of a substance is about to be initiated, the signal is preferably an acoustic, mechanical, and/or optical signal, such that this may comprise in the simplest form the outputting of a sound, a vibration or the illumination of a light source. Preferably, however, the signal comprises more detailed information regarding the flow of a substance and/or a potentially to be performed operation. For example, the sound may include a voice message, which confirms the flow of a substance at the connection point and/or provides a prompt or request for the user. Hence, by means of the signal it may be pointed to e.g. a required inspection or examination and/or an active or inactive status of the connection point or of the extracorporeal blood treatment device. The signal, in particular an optical signal, may either originate from the control unit or from the connection point or detection arrangement, however, may also be provided in a decentralized manner or at another position of the blood treatment device.

Preferably, the fluidic system comprises at least two connection points for adding substances, wherein the control unit is configured to associate a flow signal to one of the connection points and to output the signal according to the associated connecting point.

Since multiple connection points are provided and the control unit may associate the flow of a substance to a particular or specific connection point, a monitoring of the connection points or the addition of substances is also possible in a more complex system. For example, the control unit may output a signal that is specific for the respective connection point or at least for a subsystem of the blood treatment device or the fluidic system. Thereby, the user is provided with a feedback by the signal that confirms the used connection point and/or indicates a connection point to be used or operated. The user is hence precluded from a prospective mistake or error, such that the safety of the patient is further increased without requiring further cognitive efforts of the user.

Furthermore, the control unit is preferably configured to output the signal based on a comparison of the detected flow of a substance with a predetermined flow status for the connection point.

In the simplest arrangement or embodiment or when only one connection point is provided, this may already have the advantage that said connection point is not used, since a corresponding flow status during the operation of the extracorporeal blood treatment device is not intended or envisaged. For example, a connection point in the fluidic system may be arranged upstream of the extracorporeal blood treatment device, e.g. at a tube, which connects an arterial access of the patient with the blood treatment device and is only used prior to the treatment or when a treatment is interrupted, for example, to calibrate or clean the blood treatment device. Should the user perform an addition of a substance at this connection point, and hence cause a flow of a substance, this would deviate from the predefined flow status and a signal is accordingly outputted.

In particular, when multiple connection points are provided this has the advantage that for each of the connection points a flow status may be predetermined, which not only allows determining a respective usage, but optionally also includes a substance to be added. In other words, it may be provided that for a particular connection point, e.g. the addition of a particular medicament is intended, such that the outputted signal includes an information relating to the corresponding medicament.

For example, the signal may include a sound or tone as a feedback, which includes the intended medicament in a spoken form. The user is hence either provided with a confirmation that the correct substance is added or receives a corresponding warning that the performed addition does not correspond to the predetermined or intended substance. Alternatively, or in addition, the feedback may also include an indication regarding a set perfusion rate or pump rate.

Preferably, the detection arrangement is adapted or configured to comprise a respective pressure sensor and/or a flow sensor for each connection point, wherein the detection of the flow of a substance comprises the detection of a pressure and/or a flow.

Accordingly, the detection arrangement may be configured to detect or determine an actual sensor value or measurement and/or a course or development, wherein the flow of a substance is determined based on the sensor value. For example, the sensor value may vary or oscillate over a predetermined amount of time, such that a measurement of said value represents a more exact indication of the detected pressure or flow change and hence may be determined more accurately. In other words, a comparison over a predetermined amount of time may neglect or not consider small or minor fluctuations while at the same time facilitating a more accurate course, such that the detected flow of a substance may e.g. be associated to a particular performed action or operation. In particular, in this way it may be differentiated between various couplings or operation notes, such that irregularities or undesirable situations, for example, an impaired flow, or an inadvertent decoupling at a connection point may be determined.

Preferably, a display is provided and the signal that is outputted by the control unit comprises the outputting of an indication on the display.

As a display, one or more monitors or other display means may be provided, which are capable of graphically representing the indication. For example, the display may be provided in the form of a touchpad or also of a central monitor of the extracorporeal blood treatment device. Furthermore, the display may be provided as a mobile display, for example, as a mobile device, PDA, tablet, notebook or laptop, or as smart watch, wherein the mobile display is wirelessly communicatively connected to the control device, for example, via WLAN, Bluetooth, Zigbee, NFC, infrared, RFID, or the like.

The indication preferably comprises a graphical depiction of the flow of a substance, the respective connection point, the predetermined connection point, the predetermined substance, the treatment course based on a detected parameter, and/or a warning signal, depending on the configuration of the extracorporeal blood treatment device. Accordingly, the user is provided with a visual feedback, such that a potential inadvertent usage may be remedied or avoided and, at the same time, a correct treatment of the patient may be insured.

To further increase the safety of the patient, the respective or particular connection point for the addition of a substance is preferably only enabled after a user confirmation. Accordingly, at least one of the connection points comprises a closing element, preferably a clamp, wherein each of the closing elements is communicatively connected to the control unit and wherein the control unit is configured to output a user prompt or request in reaction to the presence of the signal and wherein the control unit is configured to actuate or at least partially open the closing element based on a user input and/or to output a further signal based on the user input.

For example, at each connection point a clamp may be provided, which is initially in a closed state. When the user subsequently operates or activates the connection point or provides a fluid coupling this is accordingly detected via the detected flow of a substance, such that the control unit e.g. not only outputs an indication, but also a user prompt as a signal. In a simple form, the user input only comprises a confirmation or reading confirmation or a consent with the indication, wherein the clamp is only opened after the corresponding input of the user.

However, it may also be provided that the user prompt or request requires inputting of further data, for example, the inputting of the corresponding substance to be added into the fluidic system. Although it may be provided that the clamp is also opened after such an input, the input is preferably initially compared with a predetermined flow status for the connection point—for example, also for the inputted substance—such that the clamp is either opened or remains closed, depending on the evaluation.

Accordingly, the control unit may be configured to actuate or at least partially open the closing element, when a flow signal is present and after a comparison with a predetermined flow status for the connection point.

Such a dependency of the status of the respective closing element is particularly advantageous, when multiple connection points are provided and a corresponding association of the flow of a substance to a particular or specific connection point is provided. Here, the control unit may also ensure in more complex systems that the user does not inadvertently administer liquids to the patient that are not intended or prescribed or at least not at the respective connection point. At the same time, the attention of the user may be drawn to the predetermined or intended connection point by corresponding indications, such that the required therapeutic effect is ensured and the operation of the extracorporeal blood treatment device is facilitated.

Preferably, the control unit is furthermore configured to set a flow rate, when a flow signal for the connection point is present, based on a comparison of the present flow rate with a predetermined flow rate for the connection point and/or based on a user input.

This has the advantage that the flow rate may be automatically adapted or set to the actual treatment, the treatment is not unnecessarily delayed and is performed according to a predetermined prescription or in accordance with a treatment plan. However, it may also be provided that the user input comprises an intended flow rate, which is included in the treatment plan as an administering rate, such that the user input either serves the purpose of simultaneously confirming the user prompt or constitutes a redundant safety. The inputted flow rate, or intended flow rate may also be compared with a predetermined flow status, or a treatment parameter, such that the control unit may accordingly actuate the closing element, when the input significantly deviates from e.g. a predetermined flow status, may maintain the closed state and outputs a further signal. However, when the user input essentially matches the predetermined flow status, the control unit may open the closing element and accordingly set the inputted flow rate.

The changing or setting of the flow rate may occur by actuating the closing element or also the corresponding pump. Accordingly, it may also be provided that the flow rate is directly set via the pump, wherein a flow rate equaling zero also results in not administering the added substance. Hence, the closing element may alternatively be replaced by the pump by means of a corresponding configuration of the pump and the control unit.

Furthermore, the control unit may be configured to output an alarm signal, when a flow signal is present. Thereby, the attention of the user is e.g. drawn to the presence of an error or failure, such that he or she examines or inspects the extracorporeal blood treatment device and in particular, the one or more connection points. Preferably, the alarm signal is an optical and/or acoustic alarm signal. For example, a warning light may blink or flash and/or a buzzing tone or sound may be output, when the detected flow of a substance indicates that an error or failure in the extracorporeal blood treatment device is present and the safety of the patients is potentially at risk. Preferably, the alarm signal is outputted based on a comparison of a user input with a predetermined flow status for the connection point. Accordingly, the user may be directly pointed to a deviation from a predetermined flow status, such that e.g. the error may be eliminated or the predetermined flow status may be adjusted.

To further facilitate the detection of the flow of a substance and a coupling at a respective connection point, it may furthermore be provided that the detection of a flow of a substance comprises the detection of a coupling element at the connection point, wherein the detection preferably comprises the readout of an indicator attached to the coupling element and/or a mechanical, an electromechanical, or electromagnetic switching.

For example, the detection arrangement may comprise a respective readout device in the form of a scanner or barcode scanner, which in the coupled state of an adding device, e.g. a syringe or a reservoir or container, reads out an adjacent indicator or label at a connection point. The indicator may also be read-out in the form of an RFID. Depending on the arrangement or configuration of the extracorporeal blood treatment device this function may also be included as a part of the control unit.

Alternatively, it may be provided that the coupling e.g. causes a mechanical, electromechanical, or electromagnetic switching. For example, the coupling element may comprise an electrically conductive element, which in the inserted state at a connection point causes a switching, such that a corresponding electrical signal may be read-out. Alternatively, e.g. a Hall-element may be provided, such that a corresponding signal is generated by induction, for example, when the Hall-element induces an electromagnetic signal in a winding present in the connection point, when the Hall-element is in the inserted state at a connection point.

Also, for particular connections, only matching coupling elements may be provided, such that for these connections only a limited number of substances to be added or even only one substance may be intended. For example, the coupling element and the connection point may be adapted to each other, such that these form a positive fitting connection in the coupled state, wherein this does not apply for coupling elements having a different shape. For example, the coupling element and the connection point may be formed as corresponding Poka Yoke elements. Accordingly, it may be provided that a detection of the coupling element occurs with matching elements.

Preferably, the extracorporeal blood treatment device is a hemodialysis device, a hemofiltration device, or a hemodiafiltration device, or a device for therapeutic apheresis. Accordingly, the extracorporeal blood treatment device comprises at least one dialysis filter, which separates an extracorporeal blood circuit of the patient from a dialysate circuit and wherein molecules to be removed from the blood of the patient diffuse into the dialysate via a semipermeable membrane of the dialysis filter to thereby cause a blood purification of the patient. In the case of a device for therapeutic apheresis, the extracorporeal blood treatment device comprises at least one adsorption unit, which may be combined with a dialyzer.

For the example of the hemodialysis device the at least one connection point is preferably arranged at a blood side and/or a dialysate side of the fluidic system of the extracorporeal blood treatment device. For example, when multiple connection points are present, one or more connection points may be arranged at the blood side of the fluidic system while one or more connection points may also be arranged at the dialysate side. The monitoring of the respective connection points via the respective flow status is particularly advantageous, since in the case of an inadvertent usage of a connection point a signal may be automatically outputted and the attention of the user is hence directly pointed to a false or incorrect configuration. Thereby, it may e.g. be avoided that substances that are intended for a blood side are not infused into the dialysate side and, vice versa, no substance that is intended for the dialysate side enters the blood circulation of the patient. Also, it may hence be ensured that the substance is coupled to a predetermined pump, such that a predetermined flow rate or flow rate is also met.

Preferably, the fluidic system of the extracorporeal blood treatment device comprises a disposable and the connection point is arranged at the disposable, wherein the disposable preferably comprises a container, a reservoir, a tube, a filter, a dialysis filter, an adsorber, a cassette, and/or a catheter. For example, the disposable for a hemodialysis device may be formed as a tube set, wherein the tube set comprises one or more connection points. Accordingly, the detection arrangement and the control unit may also be integrated in a disposable, such that generally a monitoring of connection points may also be performed separated from an extracorporeal blood treatment device and for other purposes, for example, infusions.

The above object is furthermore achieved by a method for monitoring a connection (20A, 20B) of an extracorporeal blood treatment device (1), preferably a hemodialysis device, a hemofiltration device, or a hemodiafiltration device, wherein the extracorporeal blood treatment device (1) comprises at least one connection point (20A, 20B) for adding substances, comprising the steps of: detecting the presence of a flow of a substance at the connection point (20A, 20B); and outputting a signal (50), when a flow of a substance is present. Preferred embodiments of the method are depicted in the present description and the Figures.

Accordingly, a method for monitoring a connection point of an extracorporeal blood treatment device, preferably a hemodialysis device, a hemofiltration device, or a hemodiafiltration device, or a device for therapeutic apheresis is suggested, wherein the extracorporeal blood treatment device comprises at least one connection point for adding substances, comprising the steps of:

detecting the presence of a flow of a substance at the connection point; and outputting a signal, when a flow of a substance is present.

The method may e.g. be performed at a fluidic system, as described in the above to monitor corresponding connection points of the fluidic system. The flow of a substance may thereby be detected by e.g. a detection arrangement and the detected flow of a substance may be received and processed or read-out by a control unit, as described in the above. In particular, all method steps may hence be performed by the blood treatment device according to the invention, such that reference is made to the corresponding structural features and a detailed description of the corresponding advantages is simultaneously at least partially avoided for reasons of redundancy.

When the extracorporeal blood treatment device comprises at least two connection points, according to the method, preferably at least two connection points are monitored, wherein the presence of a flow of a substance is associated to one of the connection points and wherein the outputted signal corresponds to the associated connection point.

Since when multiple connection points are provided the control unit may associate the flow of a substance to a particular or specific connection point, a monitoring of the connection points or the addition of substances is also possible in a more complex system. Thereby, the user is provided with a feedback by the outputting of a signal that confirms the used connection point and/or indicates a connection point to be used or operated. The user is hence precluded from a prospective mistake or error, such that the safety of the patient is further increased without requiring further cognitive efforts of the user.

Preferably, the signal is outputted based on a comparison of the detected flow of a substance with a predetermined flow status for the respective connection point.

Thereby, a signal may be outputted, when from the comparison it follows that e.g. a particular connection point should not be used, since a corresponding flow status during the operation of the extracorporeal blood treatment device is not intended.

Accordingly, such comparison may already in a simple arrangement or embodiment or when only one connection point is provided have the advantage that the safety of the patient is further improved. However, preferably multiple connection points are monitored, such that a comparison has the further advantage that not only the respective usage of the connection points is determined, but optionally it may also be checked whether a to be performed adding of a substance corresponds to a corresponding predetermined flow status. In other words, it may be provided that for a particular connection point, e.g. the addition of a particular medicament is intended, such that the outputted signal includes an information relating to the corresponding medicament.

Preferably, the detection of the flow of a substance occurs by the detection of a pressure and/or a flow by means of a respective pressure sensor and/or flow sensor. Accordingly, a flow of a substance may be determined, e.g. by means of the detection of an absolute pressure or flow, wherein the detection preferably occurs over a predetermined amount of time to include potential variations that may accordingly be considered in the detection of the flow of a substance.

Furthermore, the signal preferably comprises the presentation of an indication with a user prompt on a display, wherein a closing element provided at the connection point is actuated or at least partially opened based on a user input and/or wherein a further signal is outputted based on a user input.

Accordingly, the method may provide that e.g. a closing element initially remains in a closed state and is only released after the input of the user or after a confirmation of the user. The user is hence not only provided with feedback regarding the performed operation, but is also required to confirm said operation, preferably by means of an input corresponding to the substance.

Preferably, the closing element is actuated or at least partially opened and/or a flow rate is accordingly set in reaction to the presence of a flow of a substance or based on a comparison of the detected flow of a substance with a predetermined flow status for the connection point. For example, the input may comprise the desired flow rate, or intended flow rate. However, should the input not match a predetermined flow status, the closing elements may furthermore be maintained in the closed state, wherein in addition, a further signal may be outputted to draw the attention of the user to the non-matching condition.

It may furthermore be provided that an alarm signal, preferably an optical and/or acoustic alarm signal may be outputted based on the detected flow of a substance, preferably based on a comparison of the user input with a predetermined flow status for the connection point. Accordingly, the user is e.g. pointed to an acute failure or error, such that the user is required to inspect or examine the connection points of the fluidic system, contrary to a simple feedback.

Furthermore, the detection of a flow of a substance may comprise the detection of a coupling element at the connection point, wherein the detection preferably comprises the readout of an indicator attached to the coupling element and/or a mechanical, an electromechanical, or electromagnetic switching. Accordingly, the flow of the substance is already automatically detected upon coupling and e.g. a complex processing of a detected flow of a substance by e.g. a detection arrangement may be avoided.

BRIEF DESCRIPTION OF THE DRAWINGS

The present disclosure will be more readily appreciated by reference to the following detailed description when being considered in connection with the accompanying drawings in which.

DETAILED DESCRIPTION OF PREFERRED EMBODIMENTS

In the following, preferred embodiments will be explained with reference to the accompanying Figures. In the Figures, like elements are denoted by identical reference numerals and repeated description thereof may be omitted in order to avoid redundancies.

Figure 1:
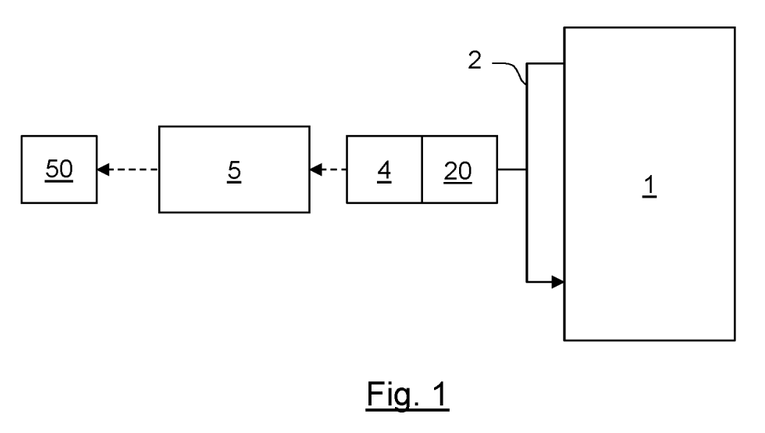
FIG. 1 shows an extracorporeal blood treatment device with a connection point.

In FIG. 1 an extracorporeal blood treatment device 1 is schematically shown, which comprises a fluidic system 2. The fluidic system 2 is coupled to an outlet and an inlet of the extracorporeal blood treatment device 1 by means of a fluid coupling and hence forms a circuit, as schematically depicted with the arrow. The fluidic system 2 may also form the entire circuit in the extracorporeal blood treatment device and may e.g. be formed in the form of a tube set that is inserted in the extracorporeal blood treatment device 1.

A connection point 20 is arranged at the fluidic system 2, which permits the adding of substances into the fluidic system 2. For example, medicaments or generally liquids with a therapeutic effect for a patient (not shown) connected to the extracorporeal blood treatment device 1 may hence be added, either directly or indirectly. Here, the connection point 20 is formed as a reservoir having a Luer lock connection, such that e.g. a syringe with a corresponding coupling may be coupled to the connection point 20 in a simple manner. The reservoir forms a cavity and may either already include a liquid or be partly filled with air to hence prevent a premature introduction of the added liquids or to build up a counter pressure, which may be displaced after a corresponding addition. Instead of a reservoir with a particular or specific connection, however, generally every connection point 20 may be chosen, for example, also a simple tube and/or a self-sealing membrane.

The connection point 20 is connected to a detection arrangement 4, such that a flow of a substance may be detected at the connection point 20 via the detection arrangement 4. Accordingly, it may e.g. be detected whether the connection point is actively used or operated or is in a free or decoupled state. This information is forwarded to a control unit 5 via a flow signal, wherein the control unit 5 is configured to output a corresponding signal 50 in reaction to the reception of a flow signal, as depicted with the dashed arrows.

According to this embodiment the signal is an optical signal in the form of a lamp or light, e.g. an LED, which is arranged at the connection point 20. Thereby, the user may be directly provided with a feedback regarding the performed action or after the processing of the detected flow of a substance, such that a performed addition of a substance or a coupling at the connection point 20 is again checked by the user or to ensure that the coupling is detected by the control unit 5. Accordingly, a simple monitoring of the performed actions or operations during and/or prior to the treatment of the patient is provided.

Figure 2:
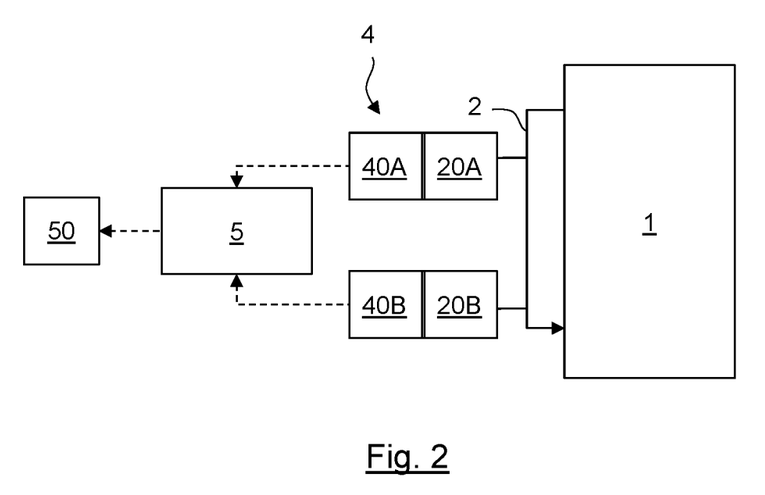
FIG. 2 shows an extracorporeal blood treatment device with multiple connection points

In the embodiment according to FIG. 2 multiple connection points 20A, 20B are provided in the fluidic system 2 of the extracorporeal blood treatment device 1. At every connection point 20A, 20B a respective detection unit of the detection arrangement 4 is provided, which are here formed as a pressure sensor 40A or flow sensor 40B. Accordingly, a flow of a substance at the connection point 20A is determined via a measurement of the pressure, wherein the detection of the pressure occurs over a predetermined amount of time and wherein the values are accordingly averaged or wherein the variation of the values is evaluated. Accordingly, also a flow of a substance at the connection point 20B is determined, wherein here it is not the pressure, but a measured flow.

The flow signals are received by the control unit 5 and are associated with a particular or specific connection point 20A, 20B, such that the control unit 5 may differentiate between the flow status of the connection point 20A and the flow status of the connection point 20B. Furthermore, predetermined values of the flow states for the respective connection points 20A, 20B are stored in the control unit 5, such that the control unit 5 may accordingly compare the flow status received via the detection signal with a nominal value or a predetermined range.

When the detected flow of a substance is within a predetermined range or corresponds to a nominal value, a corresponding signal 50 may be output as a reaction, thereby providing the user with an implicit confirmation of the correct coupling at the respective connection point 20A, 20B. However, if the flow status deviates from the predetermined flow status, a signal may accordingly be output, which indicates the incorrect or erroneous coupling to the user an may include an information regarding the correct or intended coupling.

Figure 3:
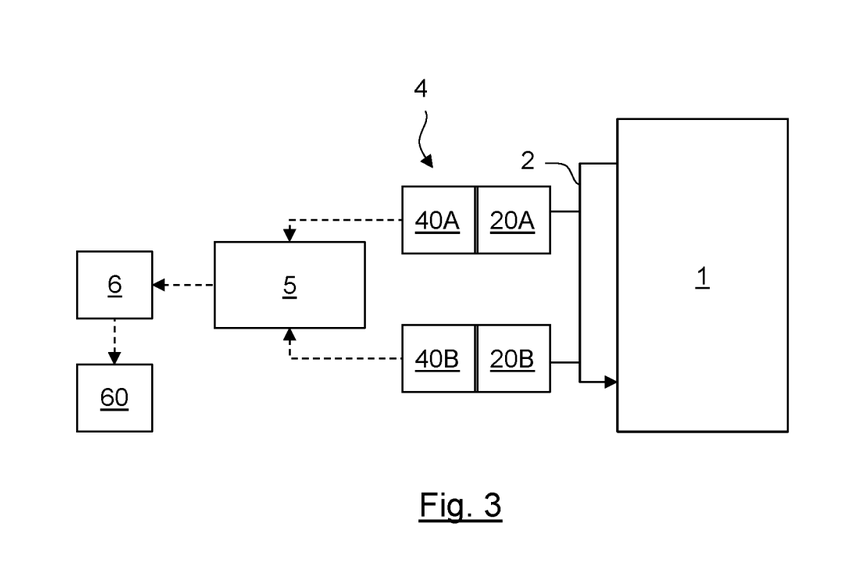
FIG. 3 shows an extracorporeal blood treatment device according to FIG. 2 with a display.

The embodiment according to FIG. 3 essentially corresponds to the extracorporeal blood treatment device of FIG. 2. In addition, the extracorporeal blood treatment device 1 comprises a display 6, which is communicatively connected or coupled to the control unit. By means of the display 6, the outputting of a signal in the form of a detailed indication 60 is possible, which includes additional information regarding the flow of a substance of the respective connection points 20A, 20B. For example, the indication 60 may represent a graphical depiction of the actual or current flow of a substance at a respective connection point 20A, 20B, for example, as an overview of the respective connection points 20A, 20B, wherein the corresponding position in the system or in the extracorporeal blood treatment device 1 is schematically depicted and is provided with a respective flow of a substance. Thereby, the indication 60 may also point to a desired or required change of a coupling, for example by means of a corresponding marking or highlighting of the respective connection points 20A, 20B.

Furthermore, the display 6 may optionally present the result of a comparison of the detected flow of a substance with a predetermined flow of a substance for the respective connection point 20A, 20B in the graphically depicted indication 60, wherein matching or erroneous values may comprise different color codes. Also, the values of the determined and/or predetermined flow states may be presented or depicted in the indication 60, such that it is indicated to the user to which extent the detected flow of a substance matches the predetermined flow of a substance.

Figure 4:
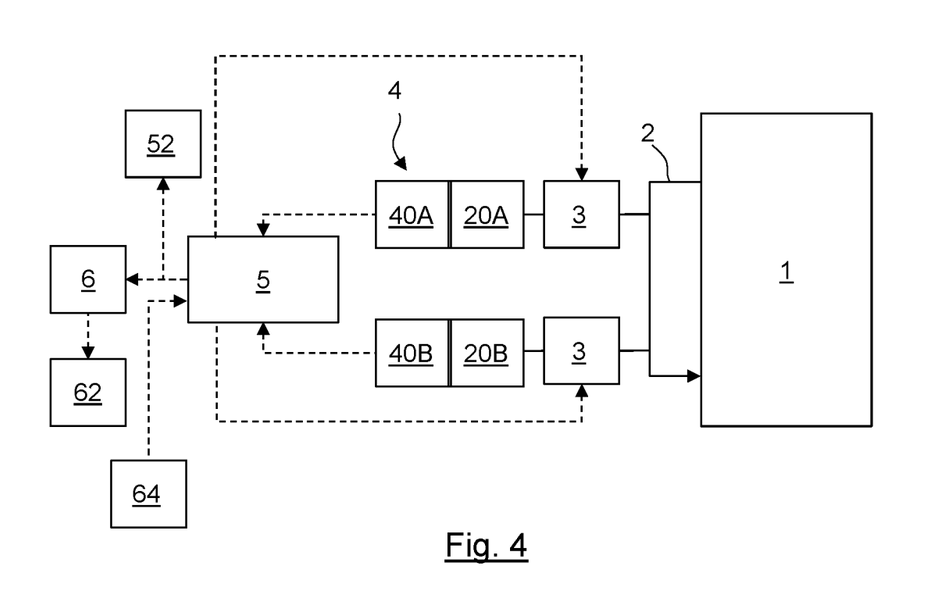
FIG. 4 shows an extracorporeal blood treatment device according to FIG. 3 with closing elements and a further user feedback.

In FIG. 4 the extracorporeal blood treatment device according to FIG. 3 is furthermore provided with closing elements 3 of a further user feedback. Each of the connection points 20A, 20B comprises a closing element 3, which provides a fluid coupling of the respective connection point 20A, 20B with a central tube of the fluidic system 2. The closing elements 3 according to the present embodiment are each formed as a clamp and avoid in the closed state that a substance added at the respective connection point 20A, 20B may flow into the fluidic system 2. The closing elements 3 are initially closed and may be actuated by the control unit 5.

When a connection point 20A, 20B is actuated or used to add a substance the flow of a substance is changed at the respective connection point 20A, 20B, which is detected or sensed by the detection arrangement 4. Since the control unit 5 associates the changed flow of a substance to a particular connection point 20A, 20B the indication on the display 6 includes a corresponding user prompt 62 or user request, which prompts the user to confirm that the used connection point 20A, 20B is indeed to be used and may also indicate a predetermined flow state, e.g. a substance that is intended for the respective connection point 20A, 20B.

The user then inputs a user input 64, which may comprise only a confirmation or also a concrete or actual input of the used substance or even a desired flow rate for the administration of the substance. The user input 64 may, as depicted, be performed directly at the control unit 5. Accordingly, the user input 64 is stored in the control unit 5 and the corresponding closing element 3 is accordingly actuated, such that e.g. a clamp is opened and/or a flow rate is automatically set.

However, should the user input 64 not match a predetermined flow status or value or deviate from a predetermined range, the control unit 5 may then output a further signal 52, e.g. an acoustic alarm or the lighting of a lamp, to draw the attention of the user to the deviation and to signalize that the respective closing element 3 has not (yet) been actuated.

The user hence receives an extended feedback or feedback, which avoids that substances are inadvertently administered or infused via the wrong or incorrect connection point 20A, 20B. Thereby, the safety of the patient is significantly increased.

Figure 5:
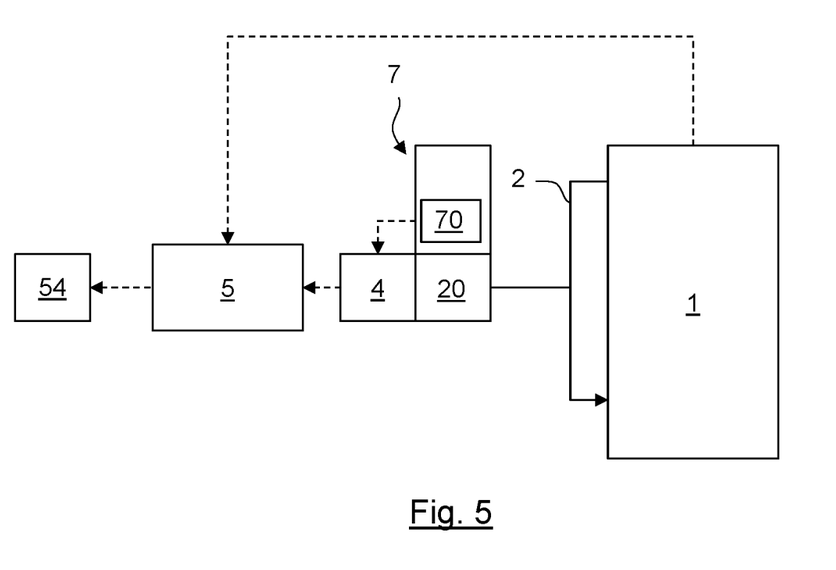
FIG. 5 shows an extracorporeal blood treatment device according to FIG. 1 with a coupled or connected coupling element.

In the extracorporeal blood treatment device 1 according to FIG. 5 the embodiment according to FIG. 1 is provided with a coupled coupling element 7. The detection arrangement 4 is thereby configured to read out an indicator 70 attached to the coupling element 7, wherein the indicator is formed in the form of an RFID. Accordingly, the detection arrangement 4 may be configured to automatically read out or receive the relevant information relating to the coupling element 7 and the corresponding substance and forward this information as a corresponding flow signal to the control unit 5.

The control unit 5 is communicatively connected to the extracorporeal blood treatment device 1, such that the control unit 5 may determine the predetermined flow of a status based on at least one detected parameter in the extracorporeal blood treatment device 1 and compare said flow status with a detected flow of a substance. If the detected flow of a substance does not match the predetermined flow status, the control unit 5 may output a corresponding alarm signal 54, such that the user is directly pointed to the coupling of an incorrect coupling element 7 and may accordingly examine or check the connection point 20 in order to remedy the failure or to couple a container with the predetermined or intended substance.

Figure 6:
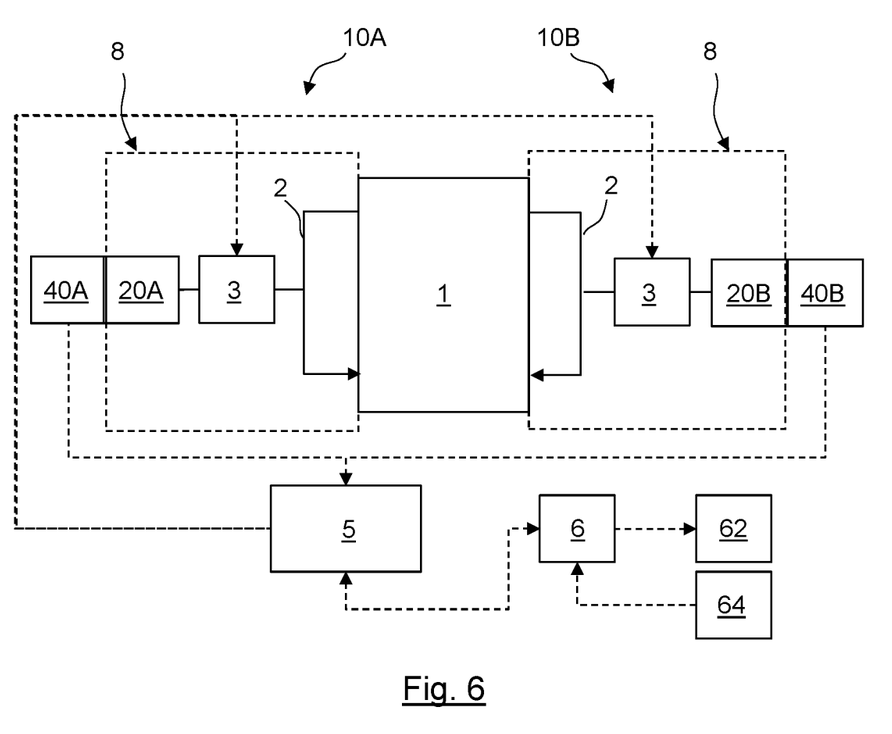
FIG. 6 shows a hemodialysis device with a blood side and a dialysate side and with coupled disposables.

The embodiment according to FIG. 6 essentially corresponds to the extracorporeal blood treatment device 1 according to FIG. 4, wherein the extracorporeal blood treatment device 2 is formed as a hemodialysis device having a blood side 10A and a dialysate side 10B and wherein the components are at least partially formed as coupled disposables 8.

Accordingly, on both sides 10A, 10B of the hemodialysis device the respective fluidic systems 2, the closing elements 3, and the connection points 20A, 20B are formed as disposables 8. The venous access and the arterial access on the blood side 10A are not shown.

At respective connection points 20A, 20B of the disposables 8 the sensors 40A, 40B are accordingly coupled, such that the control unit 5 may receive and process or evaluate flow signals regarding the detected flow of a substance. Furthermore, the control unit 5 is communicatively connected with the respective closing elements 3, such that the control unit 5, as in FIG. 4, may actuate the respective closing elements 3 based on a user input 64. The inputting of the user input 64 is performed according this embodiment on the display 6, which allows or enables the inputting of the user input 64, for example, when this is accordingly formed as a touchpad or comprises a keyboard. The interface between the display 6 and the control unit 5 allows in this case a communication in both directions, such that the user input 64 is also forwarded to the control unit 5.

Thereby, the control unit 5 may monitor the connection points 20A, 20B of the respective side 10A, 10B and hence may differentiate between the sides 10A, 10B, such that the particular association of the connection points 20A, 20B and the required user input 64 provide an increased safety of the patient and at the same time a correct functioning according the therapeutic prescriptions may be maintained.

Where applicable, all individual features depicted in the embodiments may be combined and/or replaced without leaving the scope of the invention.

LIST OF REFERENCE NUMERALS

1 Extracorporeal blood treatment device
10A Blood side
10B Dialysate side
2 Fluidic system
20 Connection point
20A Connection point
20B Connection point
3 Closing element
4 Detection arrangement
40A Pressure sensor
40B Flow sensor
5 Control unit
50 Signal
52 Signal
54 Alarm signal
6 Display
60 Indication
62 User prompt
64 User input
7 Coupling element
70 Indicator
8 Disposable

The invention claimed is:

1. Extracorporeal blood treatment device comprising:
a fluidic system having at least two connection points for adding substances;
a detection arrangement for detecting a flow of a substance at each of the connection points, wherein the detection arrangement is configured to generate a flow signal, when a flow of a substance is detected at one of the connection points;
a control unit communicatively connected to the detection arrangement and configured to associate the flow signal to one of the connection points and to output a signal according to the associated connecting point in reaction to a received flow signal,
wherein at least one of the connection points comprises a closing element communicatively connected to the control unit, wherein the control unit is configured to output a user prompt in reaction to the presence of the flow signal, wherein the signal is output during continuous presence of a flow signal indicating one of the connection points being used, and wherein the control unit is configured to actuate or at least partially open the closing element based on a user confirmation in response to the user prompt.

2. Extracorporeal blood treatment device according to claim 1, characterized in that each of the connecting points is specific for a subsystem of the extracorporeal blood treatment device or the fluidic system.

3. Extracorporeal blood treatment device according to claim 1, characterized in that the detection arrangement comprises a respective pressure sensor and/or a flow sensor for each connection point and wherein the detection of the flow of a substance comprises the detection of a pressure and/or a flow.

4. Extracorporeal blood treatment device according to claim 1, characterized in that a display is provided and wherein the signal that is outputted by the control unit comprises the outputting of an indication on the display.

5. Extracorporeal blood treatment device according to claim 1, characterized in that the closing element is a clamp.

6. Extracorporeal blood treatment device according to claim 5, characterized in that the control unit is configured to actuate or at least partially open the closing element, when a flow signal is present and after a comparison with a predetermined flow status for the connection points.

7. Extracorporeal blood treatment device according to claim 5, characterized in that the control unit is configured to set a flow rate, when a flow signal for each of the connection points is present, based on a comparison of the present flow rate with a predetermined flow rate for each of the connection points and/or based on a user input.

8. Extracorporeal blood treatment device according to claim 1, characterized in that the control unit is configured to output an alarm signal, when a flow signal is present.

9. Extracorporeal blood treatment device according to claim 1, characterized in that the detection of a flow of a substance comprises the detection of a coupling element at each of the connection points.

10. Extracorporeal blood treatment device according to claim 1, characterized in that the fluidic system comprises a disposable and wherein the connection are arranged at the disposable.

11. Extracorporeal blood treatment device according to claim 1, characterized in that the control unit is configured to output at least one of an optical alarm signal and an acoustic alarm signal, when a flow signal is present, based on a comparison of a user input with a predetermined flow status for the connection point.

12. Extracorporeal blood treatment device according to claim 1, characterized in that the detection of a flow of a substance comprises the detection of a coupling element at each of the connection points, wherein the detection comprises at least one of the readout of an indicator attached to the coupling element and a mechanical, electromechanical, or electromagnetic switching.

13. Extracorporeal blood treatment device according to claim 1 selected from the group consisting of a hemodialysis device, a hemofiltration device and a hemodiafiltration device, characterized in that the fluidic system comprises a disposable and wherein the connection points are arranged at the disposable, wherein the disposable comprises at least one of a container, a reservoir, a tube, a filter, and a dialysis filter, and at least one of an adsorption unit, a cassette, and a catheter.

14. Extracorporeal blood treatment device according to claim 1 selected from the group consisting of a hemodialysis device, hemofiltration device, hemodiafiltration device, and a device for therapeutic apheresis.

* * * * *